(12) United States Patent
Ho et al.

(10) Patent No.: US 7,624,735 B2
(45) Date of Patent: Dec. 1, 2009

(54) CHEEK-MOUNTED PATIENT INTERFACE

(75) Inventors: Peter Chi Fai Ho, Pittsburgh, PA (US); Lance Busch, Trafford, PA (US); Jerome Matula, Jr., Monroeville, PA (US)

(73) Assignee: Respironics Respiratory Drug Delivery (UK) Ltd, West Sussex (GB)

( * ) Notice: Subject to any disclaimer, the term of this patent is extended or adjusted under 35 U.S.C. 154(b) by 415 days.

(21) Appl. No.: 11/228,832

(22) Filed: Sep. 16, 2005

(65) Prior Publication Data
US 2006/0060200 A1  Mar. 23, 2006

Related U.S. Application Data

(60) Provisional application No. 60/611,867, filed on Sep. 21, 2004.

(51) Int. Cl.
*A62B 18/08* (2006.01)

(52) U.S. Cl. .................... 128/207.11; 128/205.25; 128/206.11; 128/206.12; 128/206.13; 128/206.14; 128/206.16; 128/206.17; 128/206.18; 128/206.19; 128/206.21; 128/206.23; 128/206.24; 128/206.25; 128/206.26; 128/206.27; 128/206.28; 128/206.29; 128/207.13; 128/207.17; 128/207.18

(58) Field of Classification Search ............ 128/205.25, 128/206.11–206.14, 206.16–206.19, 206.21, 128/206.23–206.29, 207.11, 207.13, 207.17, 128/207.18
See application file for complete search history.

(56) References Cited

U.S. PATENT DOCUMENTS

| 6,019,101 | A | 2/2000 | Cotner et al. |
|---|---|---|---|
| 6,119,694 | A | 9/2000 | Correa et al. |
| 6,615,830 | B1 | 9/2003 | Serowski et al. |
| 6,651,663 | B2 | 11/2003 | Barnett et al. |
| 2003/0196655 | A1 | 10/2003 | Ging et al. |
| 2003/0196656 | A1 | 10/2003 | Moore et al. |
| 2003/0196657 | A1 | 10/2003 | Ging et al. |
| 2003/0196658 | A1 | 10/2003 | Ging et al. |
| 2003/0196662 | A1 | 10/2003 | Ging et al. |
| 2004/0045551 | A1 | 3/2004 | Eaton et al. |
| 2004/0112385 | A1 | 6/2004 | Drew et al. |
| 2006/0231103 | A1* | 10/2006 | Matula et al. .......... 128/207.13 |

OTHER PUBLICATIONS

Respironics, Inc., "the comfort series™", ComfortGel™ Mask, 2003.
Resmed Ltd., "Mirage® Vista™", 2002.

* cited by examiner

*Primary Examiner*—Patricia M Bianco
*Assistant Examiner*—Nihir Patel
(74) *Attorney, Agent, or Firm*—Timothy A. Nathan

(57) ABSTRACT

A patient interface that includes a support body having a cushion and cheek interfaces. Collectively, the cushion and cheek interfaces operate to distribute compressive forces exerted on the user's face. The support body of the patient interface is constructed from a flexible material to impart additional adjustability to the cheek interfaces. The support body also has arcuate eyelets designed to provide a hinge between the headgear assembly and the support body.

17 Claims, 4 Drawing Sheets

CHEEK-MOUNTED PATIENT INTERFACE

CROSS-REFERENCE TO RELATED APPLICATIONS

Under the provisions of 35 U.S.C. § 119(e), this application claims the benefit of U.S. Provisional Application Ser. No. 60/611,867, filed Sep. 21, 2004.

BACKGROUND OF THE INVENTION

1. Field of the Invention

The present invention pertains to a respiratory patient interface used to deliver gas to a user and a method for using the same. In particular, the present invention is related to a flexible, cheek mounted patient interface that includes self-adjustment features to enhance the patient's comfort.

2. Description of the Related Art

A variety of delivery systems are known that provide gas at positive pressure for consumption by the patient. The uses and applications of such systems vary. Some such systems have been developed for the treatment of sleep apnea and other sleep related disorders.

Sleep apnea syndrome results in episodic upper airway obstruction during sleep. As a consequence, there is repeated interruption of sleep in the patient. Positive airway pressure (PAP) devices have been developed to treat this disorder. A typical PAP device comprises a flow generator (e.g., a blower) that delivers gas via a delivery conduit to a patient interface, such as a mask. It is also known to deliver the PAP pressure as a continuous positive airway pressure (CPAP), a variable airway pressure, such as a bi-level pressure that varies with the patient's respiratory cycle, or an auto-titrating pressure that varies with the monitored condition of the patient. Pressure support therapies are also provided to treat other medical and respiratory disorders, such as Cheynes-Stokes respiration, congestive heart failure, and stroke.

Mask development has generally involved balancing of two competing goals: secure attachment to create an airtight seal in order to facilitate the required positive airway pressure, and comfort to the user in order to maximize patient compliance. An airtight seal can be achieved by tightening the mask down firmly against the patient's face. However, this solution oftentimes results in discomfort to the user due to relatively high strapping forces needed to ensure a secure seal against the patient and less than satisfactory patient compliance. Alternatively, the mask may be fit loosely on the patient's face to enhance comfort. However, the effectiveness of the mask may be compromised if it is too loose.

A variety of masks have been suggested in the art seeking to address one or both of the above noted issues. In order to enhance comfort and provide an adequate seal, several low contact masks have been suggested which minimize the contact area between the patient and the mask. For instance, U.S. Pat. No. 6,615,830 ("the '830 patent") discloses a mask that includes a rigid shell having an aperture and a seal member connected to the shell and adapted to sealingly engage the region about the patient's nose. The seal has an internal cavity in fluid communication with the aperture of the rigid shell. The aperture of the rigid shell, in turn, is connected via a coupling to the distal end of a gas delivery conduit. In order to deliver gas to the patient, the proximal end of the conduit is connected to the positive airway pressure device, i.e., a flow generator. In order to secure the mask to the user, three radially extending ears are spaced about the rigid shell. Each ear provides at least one eyelet sized to receive a strap that encircles the patient's head to secure the nasal mask in place.

Although masks manufactured in accordance with the teachings of the '830 patent have performed well in the industry, such masks can still be further improved upon. To provide an adequate seal with the patient's face, the headgear assembly must be firmly tightened to pull the mask down about the patient's nose region. As the mask is tightened, the force exerted by the headgear is concentrated about the patient's nose and may be deemed uncomfortable by some patients. Moreover, this mask does not provide easy adjustability. The location of contact between the sealing member and the patient is fixed as a result of using a rigid collar and an immovable seal.

In order to further advance the art, other mask assemblies have been suggested that utilize separate regions of contact on the patient's face to distribute the force exerted by the headgear between the patient's forehead and nasal region. For instance, one such mask is described in published U.S. Patent Appln. No. US-2004-0045551-A1 ("the '551 application"). Similar to the previously described mask, the mask taught by the '551 application has a rigid shell with an aperture that engages an end of the coupling. A seal member, also referred to as a cushion, is attached to the shell and engages the region about the patient's nose. Extending from the shell is a pair of ears configured to be secured to the headgear via eyelets.

One distinguishing feature of this mask as compared to the mask disclosed in the '830 patent is that it includes a forehead stabilizer that contacts the patient's forehead. The stabilizer includes an arm that extends radially outwardly from the nasal portion of the mask. A pad support is pivotably attached to the end portion of a mechanically adjustable arm so that the pad can be properly located on the forehead of the patient. The pad support has an inner surface to which a pad is removably attached. The pad is manufactured from a flexible material that is capable of conforming to the contours of the patient's head thus enhancing comfort.

This mask provides several advantages over the prior art. For instance, it disperses the load over multiple locations on the user, i.e., the nasal region and the forehead region. By engaging the patient's face in multiple locations, the force exerted by the headgear is dispersed about the patient's face, thus enhancing the comfort associated with using this device. In addition, having multiple regions of contact with the patient's face is more secure than when the mask only engages one region of the user's face.

Although such devices have substantially advanced the art, addition improvements are still possible. For instance, the rigid construction of the shell, ears, and arm of this mask prevents it from being easily adjusted to fit different patients. The patient, or a caregiver, must manipulate various mechanical features in order to adjust this mask or multiple different sizes need to be constructed. Secondly, although having two separate engagement locations provides superior securement of the device compared with single point engagement, even this mask may move around on the patient's face unless the headgear is firmly tightened thus potentially resulting in discomfort to some patients. In order to properly fit, this nasal mask requires some manipulation by the patient or a caregiver.

Additional masks have been suggested to address the competing goals of comfort and stability. One such nasal mask, which is described in U.S. Pat. No. 6,019,101 ("the '101 patent") has a flexible shell defined by a contoured portion circumscribing the nasal region of the patient with a pair of integral side wings designed to extend laterally over the patient's cheeks. A large gel-filled seal is disposed on the interior of the shell to provide a large airtight contact area with the patient's face. Even though this mask operates effectively for its intended purpose, it also has several disadvantages. This mask utilizes a large heavy seal attached to the rear surface of the shell in order to both seal and disperse compression forces about the nasal region of the user. In order to achieve both of these functions adequately, a large thick seal is required. Secondly, the seal is fixed to the shell thus preventing the seal from being adjusted to accommodate different users. Further, the seal abuts the face of the user about the nasal region thus concentrating a majority of the force exerted by the headgear in this region similar to the situation presented by the mask described in the '830 patent.

In light of the above, it is apparent that further advancements in the mask art would be desirable. For instance, it would be desirable to have a mask that provides stable and secure engagement about the patient's nasal region in order to maintain fluid communication with the PAP device. It would also be desirable to have a device that is configured to enhance the comfort experienced by the patient. In addition, it would also be desirable to have a nasal mask which can self-adjust so that a single device can adapt to a variety of different facial contours without manipulation by the user or caregiver. It would be further desirable to have a device that is configured to reduce the number of complex mechanical parts to reduce wear. Still further, it would be desirable to have a mask that avoids providing any structural features near the patient's eyes. This is particularly important for patient's who desire to where glasses while wearing the mask and for patient's that tend to feel claustrophobic when a structure is provided at or near their eyes. Avoiding the ocular area also eliminates or avoids the leakage of gas into the user's eyes, which can cause great discomfort. Finally, it would be desirable to have a mask that accomplishes these functions while also providing a relatively high degree of adjustability, so that a common mask style or configuration can be fitted to a variety of patients with deferent facial characteristics.

SUMMARY OF THE INVENTION

In accordance with the broad teachings of the invention a patient interface is disclosed which is configured to deliver gas to a user. The interface includes a cushion having a centrally disposed aperture. The aperture opens to an internal cavity that is configured to receive the nose of the user. A support body is attached to the cushion to provide structural support. The support body also has a centrally disposed aperture in communication with the interior of the cushion via the centrally disposed aperture of the cushion.

The patient interface of the present invention also includes two discrete cheek interfaces attached to the support body. Each of the cheek interfaces are designed to positively engage a corresponding cheek of the user so that it is securely affixed. As discrete components, each cheek interface may be moved independently relative to one another so that the patient interface may be easily customized for use with different users. To hold the patient interface in place about the patient's nose, the present invention also includes a headgear assembly which pulls the mask securely against the face of the user. The compressive forces exerted by the headgear assembly are distributed between the patient interface cushion and the discrete cheek interfaces thus providing three separate points of contact with the user's face.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
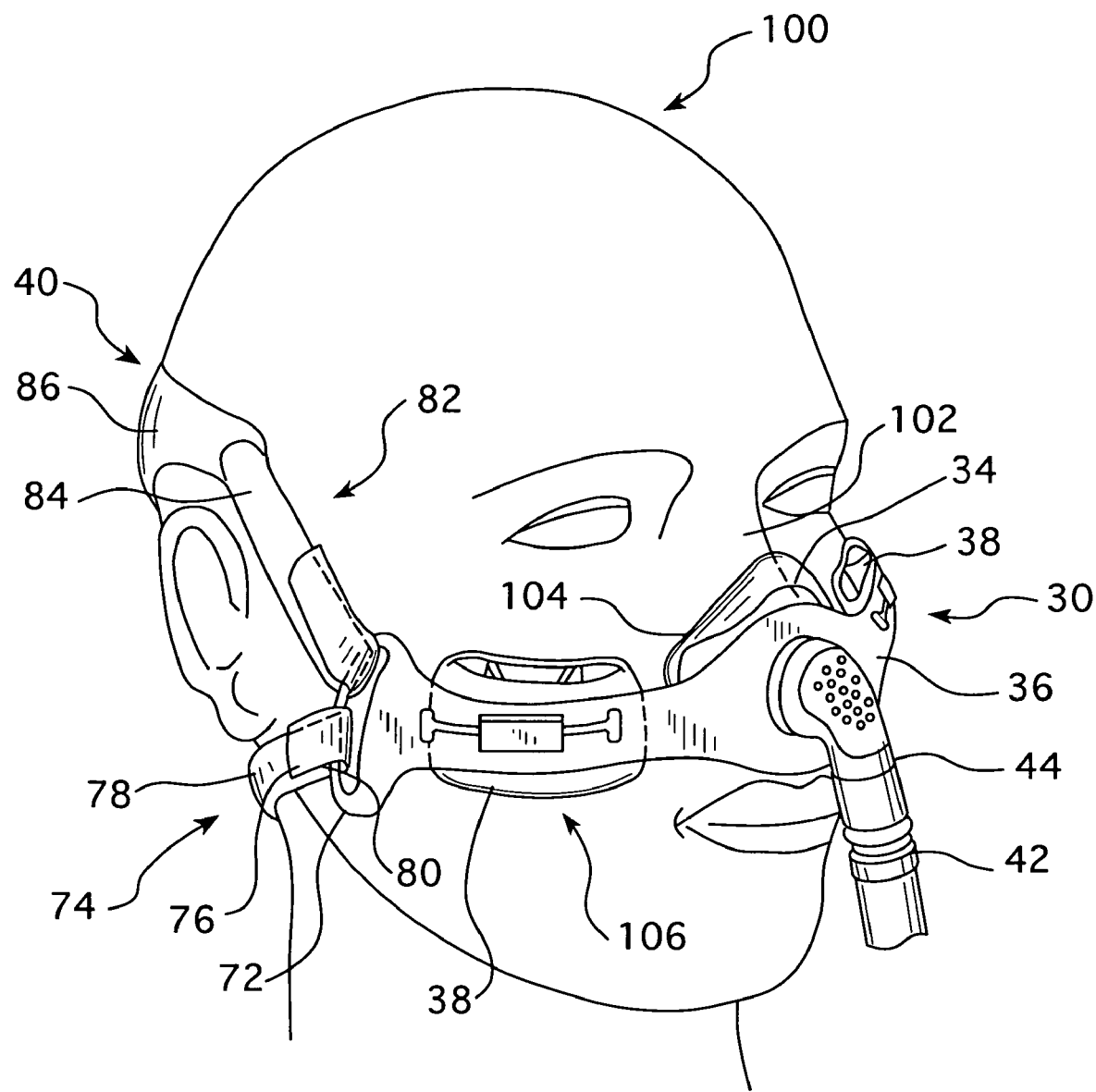
FIG. 1 is a front perspective view of the patient interface of the present invention located on the face of a user.

FIG. 1 schematically illustrates an exemplary embodiment of a patient interface 30 according to the principles of the present invention. As shown in FIG. 1, patient interface 30 is configured to be securely mated to a user 100 in order to deliver gas at a positive pressure for consumption by the user. Patient Interface 30 includes a user interface cushion 34 supported by a support body 36 and a two cheek interfaces 38. The patient interface is held in place by a headgear assembly 40. Gas is delivered to mask assembly 30 via a conduit 42 connected between a gas compressor, not shown, and a coupling 44 attached to the support body 36. Coupling 44 may have a variety of configurations. However, in an exemplary embodiment of the present invention, as shown in FIG. 1, coupling 44 has an L-shaped configuration.

Figure 2:
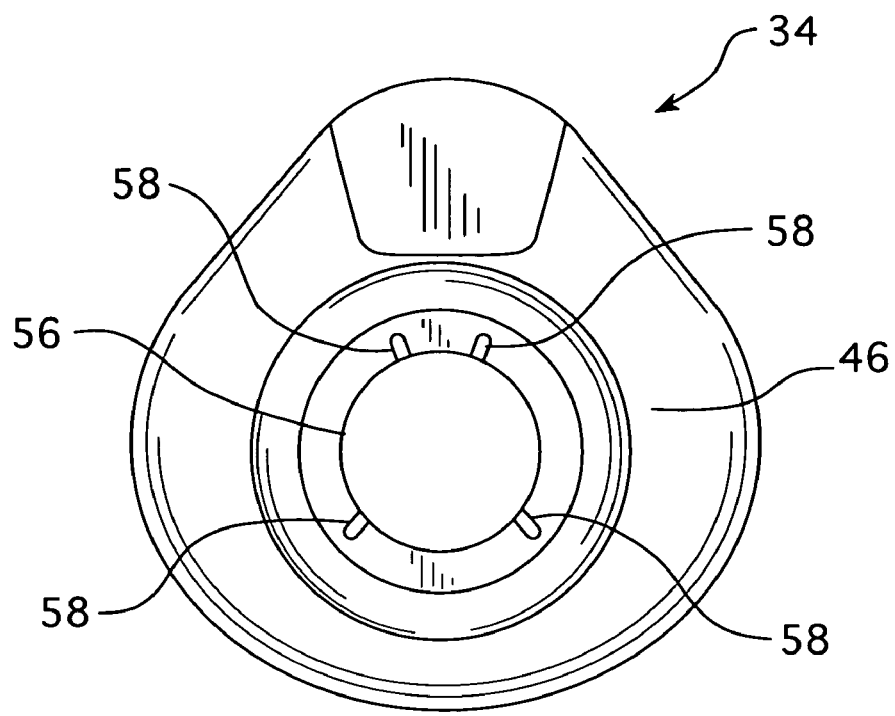
FIG. 2 is a rear elevational view of a user interface cushion of the patient interface.
Figure 3:
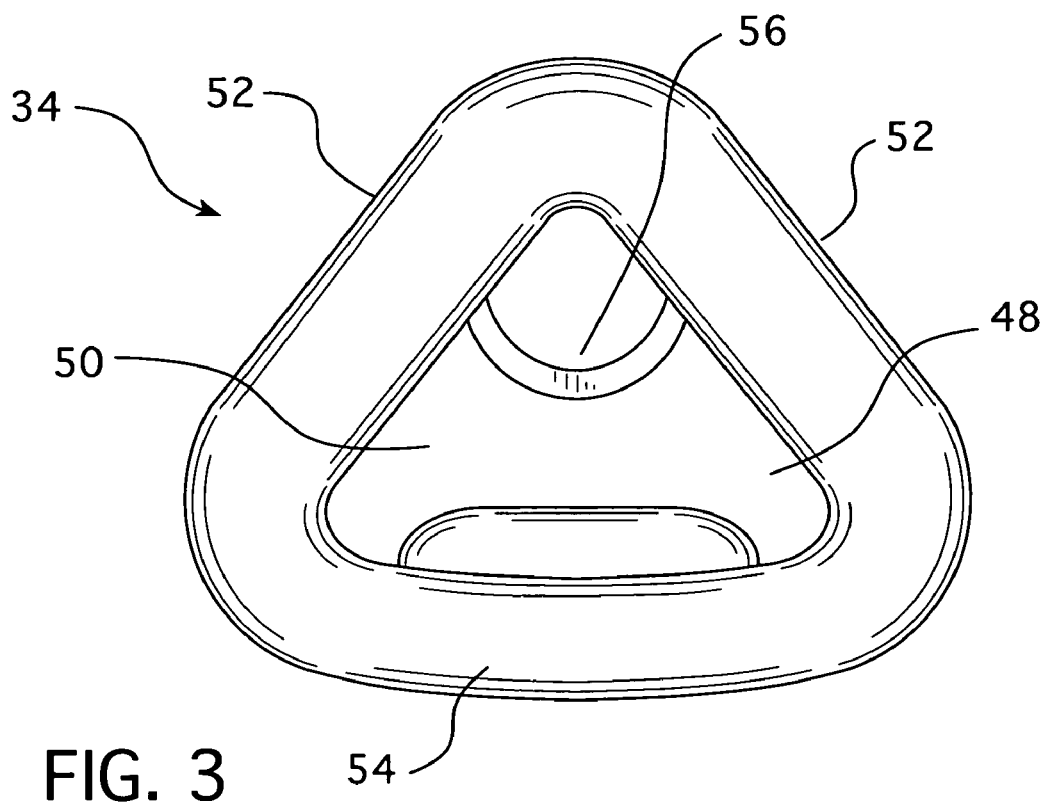
FIG. 3 is a front elevational view of the user interface cushion of FIG. 2.

Turning to FIGS. 2 and 3, the present invention utilizes a contemporary interface cushion. An example of such a cushion is described in detail in U.S. Pat. No. 6,651,663 the teachings of which are hereby incorporated by reference in its entirety. User interface cushion 34 has a generally pyramidal configuration and is defined by an outer surface 46 and an inner surface 48. The inner surface, in turn, defines a cavity 50 for receipt of at least a portion of the user's nose 102. User interface cushion 34 abuts against a nasal region 104 around the user's nose 102 along a pair of side edges 52 and a lower edge 54.

To provide an acceptable seal with the user, user interface cushion 34 is constructed from any flexible airtight material capable of being compressed to create a seal. Several materials are commonly used in the art to create a seal such as silicone, gel, or foam. However, other similar materials may be used without departing from the scope of the invention. User interface cushion 34 also includes an aperture 56 with grooves 58 thereabout. Grooves 58 assist in aligning user interface cushion 34 with support body 36, as described in further detail below.

Figure 4:
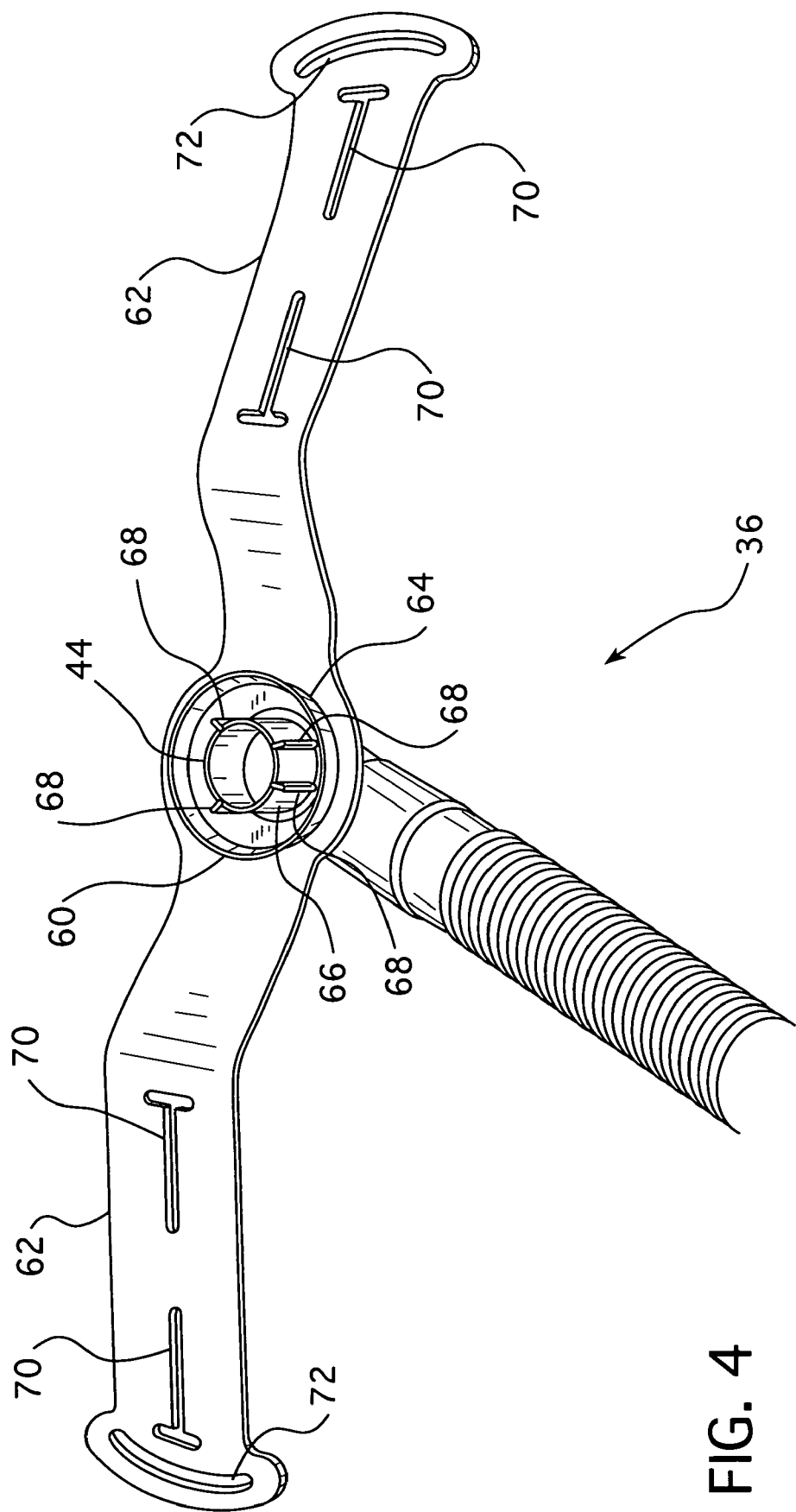
FIG. 4 is a front perspective view of the support body of the patient interface.

With particular reference to FIG. 4, support body 36 of the present invention has a central portion 60 and two wings 62 extending from the central portion 60. Support body 36 may be constructed from a variety of materials. Preferably, support body 36 is constructed from a flexible material that is capable of being deformed such as polypropylene, polyethylene or other similar materials. The support body has a central aperture 64 into which coupling 44 is fitted. As seen in FIG. 4, coupling 44 terminates at a cylindrical portion 66 having ribs 68 extending outwardly therefrom. Ribs 68 are located about cylindrical portion 66 and correspond with slots 58 formed in cushion 34 to maintain alignment between coupling 44 and cushion 34. In one embodiment, support body 36 and coupling 44 are formed as separate members and sealed together. Alternatively, the support body and coupling are integrally formed together.

Each of the wings of support body 36 has elongate slots 70 designed to provide sliding engagement between the support body and the corresponding cheek interface 38, so that the location of the cheek interface relative to the support body may be adjusted to accommodate the facial features of a particular user 100 and properly register on the correct cheek region of the user. Each of the wings terminates at an eyelet 72. Returning to FIG. 1, the eyelets are used as anchor points to which the headgear assembly 40 is attached.

Headgear assembly 40 includes a lower strap 74 fitted about the user's head 108. Lower strap 74 has a pair of end portions 76. Each of the end portions 76 is threaded through a corresponding eyelet 72 and secured back to a median portion 78 of lower strap 74, thus creating a loop 80 about the corresponding eyelet 72. Headgear assembly 40 also includes an upper strap 82. The upper strap includes a pair of side straps 84 joined to a rear web 86. The side straps are also threaded about eyelet 72 to secure the upper strap 82 to the support body 36. Alternatively, upper strap 82 and lower strap 74 may be formed together as a single member thus reducing the number of pieces used to form the headgear assembly 40. In either embodiment, lower strap 74 and upper strap 82 are threaded through the eyelets 72. The straps can be constructed of any suitable all-purpose strap material such as the multi-purpose strap material sold under the trademark VEL-STRETCH™ by Velcro Industries B.V.

One unique feature of the present invention is that eyelets 72 are arcuate in shape. This arcuate configuration allows for upper straps 82 and lower straps 74 to easily slide within the eyelet to create a pseudo-hinge or pivot point between headgear assembly 40 and support body 36. As patient interface 30 is secured to the user, straps 74, 82 are permitted to self-adjust relative to the support body by sliding within the eyelets, so that the user does not have to actively adjust straps 74, 82. Instead, straps 74, 82 passively adjust to accommodate the user.

Figure 5:
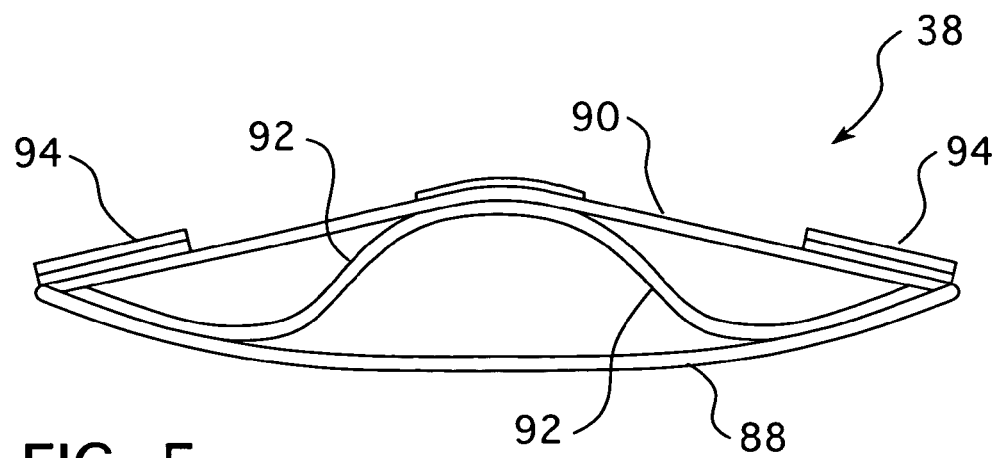
FIG. 5 is a top plan view of a cheek interface of the present invention.

Patient interface 30 of the present invention contacts the user 100 at three distinct points. This is achieved through the use of two discrete cheek interfaces 38 and user interface cushion 34. As seen in FIG. 5, each cheek interface 38 has an outer surface 88 adapted to contact the user's cheek region 106 and an inner surface 90. Located between outer surface 88 and inner surface 90 are ribs 92. The ribs are sized and located to allow each cheek interface 38 to comfortably conform to the contours of the user's cheek region 106.

Figure 6:
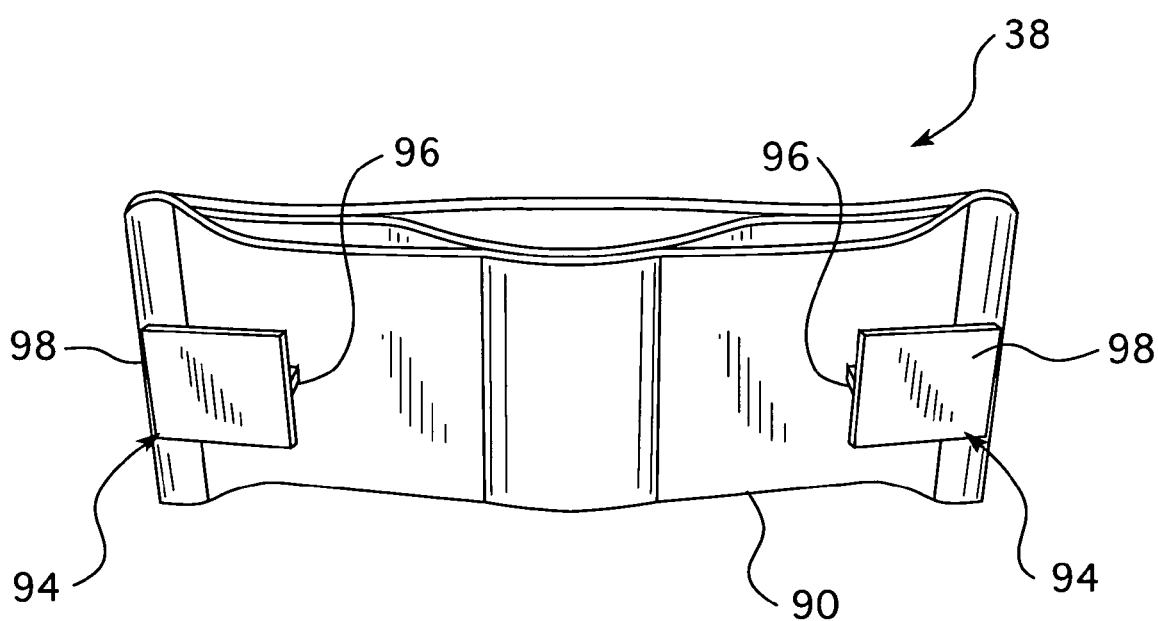
FIG. 6 is a rear perspective view of the cheek interface of FIG. 5.

As best appreciated with reference to FIG. 6, each cheek interface 38 is slidably engaged to support body 36 via barbs 94. Each barb 94 includes a stem portion 96 and a bearing surface 98. Each bearing surface 98 is forced through the corresponding elongate slot 70, as seen in FIGS. 1 and 4, to capture stem 96. Cheek interface 38 may be actively adjusted by the user through sliding cheek interface 38 to the appropriate location along the length of each elongate slot 70. Once properly located, friction between cheek interface 38 and support body 36 retains the cheek interface 38 in position. The adjustability of cheek interface 38 allows for a single patient interface 30 to be used with multiple different users and permits customization to accommodate various users.

Another unique advantage of the present invention is that by virtue of being discrete elements, cheek interfaces 38 can be moved independently relative to one another. In combination with the flexibility of support body 36, the patient interface can be easily adjusted to precisely locate each cheek interface 38 in the optimum location for a particular user 100 to more evenly distribute the compression forces. Because, cheek interfaces 38 of the present invention serve only as load bearing members, rather than both load bearing and sealing functions, cheek interfaces 38 can be appropriately sized and shaped to achieve their intended purpose rather than being oversized in order to adequately achieve both sealing and load bearing functions.

To use the present invention, the user, or a caregiver, will adjust cheek interfaces 38 such that they are properly located to engage the appropriate portion of the user's cheek region. Next the user, or caregiver, can place the mask assembly on the user such that user's nose 102 extends into cavity 50. The user will then position cheek interfaces 38 on the user's cheek regions 106 in place by tightening the headgear assembly. Once the mask assembly is securely affixed to the user's head 108, breathing gas can then be administered to the user.

While the present invention has been described above as having a cushion that encapsulates the nasal region, it is to be understood that the present invention contemplates using other types of devices in conjunction with support body 36. For example, larger cushions that encapsulate the nose and mouth can be attached to the support body. Conversely, smaller cushions, or nasal prongs, that seal in or near the nares can be supported by the support body. In short, any interface suitable for sealing against the user can be used in the mask assembly of the present invention.

It should also be understood that the present invention is not intended to be limited to a particular material for user interface cushion 34 or cheek interfaces 38. For example, these components can be formed from a silicone, plastic, rubber, foam, gel, or any other material or combination of materials that provides a sufficiently comfortable interface with the user's skin.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A patient interface comprising:

a cushion having a first aperture;

a support body attached to the cushion having a second aperture in communication with the first centrally disposed aperture of the cushion;

at least one cheek interface attached to the support body, the cheek interface includes an inner surface and an outer surface, the cheek interface further includes a structure extending between the inner surface and the outer surface, the structure comprising a plurality of flexible ribs disposed within the structure such that installation of the cheek interface on the face of a patient, with the inner surface of the cheek interface in contact with the face of the patient, causes the flexible ribs to flexibly deform such that the inner surface of the cheek interface conforms to the contours of the face of the patient that the inner surface contacts; and a headgear assembly connected to the support body.

2. The patient interface as described in claim 1, wherein the support body is constructed from a flexible material.

3. The patient interface as described in claim 2, wherein the flexible material is selected from a group consisting of polyethylene or polypropylene.

4. The patient interface as described in claim 1, wherein the support body comprises:
 a central portion; and
 at least one wing extending from the central portion.

5. The patient interface as described in claim 4, wherein the wing includes at least one eyelet, the eyelet having an arcuate shape.

6. The patient interface as recited in claim 1, wherein the cheek interface is selected from a group of materials consisting of silicone, foam, or gel.

7. A patient interface comprising:
 a cushion having a first aperture;
 a support body attached to the cushion having a second aperture in communication with the first aperture of the cushion, the support body including a central portion and a plurality of wings extending from the central portion, each wing having an elongate slot, each wing includes at least one eyelet, the eyelet having an arcuate shape, the support body is constructed from a flexible material;
 a plurality of cheek interfaces, each cheek interface being attached to one of the wings, each cheek interface having a projecting barb fitted through the elongate slot to provide sliding engagement along each elongate slot such that the cheek interfaces are slidably adjustable relative to the support body; and
 a headgear assembly connected to the support body.

8. A patient interface comprising:
 a cushion having a first aperture;
 a support body attached to the cushion having a second aperture in communication with the first aperture of the cushion, the support body including a central portion and a plurality of wings extending from the central portion, each wing having an elongate slot, each wing includes at least one eyelet, the eyelet having an arcuate shape;
 a plurality of cheek interfaces, each cheek interface being attached to one of the wings, each cheek interface having a projecting barb fitted through the elongate slot to provide sliding engagement along each elongate slot such that the cheek interfaces are slidably adjustable relative to the support body; and
 a headgear assembly connected to the support body.

9. The patient interface as recited in claim 8, wherein each cheek interface further comprises:
 an inner surface;
 an outer surface; and
 a projecting barb extending from the inner surface.

10. The patient interface as recited in claim 9, wherein each cheek interface further comprises at least one rib extending between the inner surface and the outer surface.

11. The patient interface as recited in claim 10, wherein the cheek interface is selected from a group of materials consisting of foam, gel or plastic.

12. The patient interface as recited in claim 10, wherein the support body further comprises at least one wing having an elongate slot for receipt of the corresponding projecting barb of the cheek interface.

13. A patient interface comprising:
 a cushion having a first aperture;
 a support body attached to the cushion having a second aperture in communication with the first aperture of the cushion, the support body including a central portion and a plurality of wings extending from the central portion, each wing having an elongate slot;
 a plurality of cheek interfaces, each cheek interface being attached to one of the wings, each cheek interface having a projecting barb fitted through the elongate slot to provide sliding engagement along each elongate slot such that the cheek interfaces slidably adjustable relative to the support body, each cheek interface includes an inner surface and an outer surface, the cheek interface further includes a structure extending between the inner surface and the outer surface, the structure comprising a plurality of flexible ribs disposed within the structure such that installation of the cheek interface on the face of a patient, with the inner surface of the cheek interface in contact with the face of the patient, causes the flexible ribs to flexibly deform such that the inner surface of the cheek interface conforms to the contours of the face of the patient that the inner surface contacts; and
 a headgear assembly connected to the support body.

14. The patient interface as recited in claim 13, wherein the cheek interface is selected from a group of materials consisting of foam, gel or plastic.

15. The patient interface as described in claim 13, wherein the support body is constructed from a flexible material.

16. The patient interface as described in claim 15, wherein the flexible material is selected from a group consisting of polyethylene or polypropylene.

17. The patient interface as described in claim 13, wherein the wing includes at least one eyelet, the eyelet having an arcuate shape.

* * * * *